US00PP31645P2

(12) United States Plant Patent
Sproul

(10) Patent No.: US PP31,645 P2
(45) Date of Patent: Apr. 14, 2020

(54) MINIATURE ROSE PLANT NAMED 'SPROULSUN'

(50) Latin Name: *Rosa hybrida*
Varietal Denomination: Sproulsun

(71) Applicant: The Conard-Pyle Company, West Grove, PA (US)

(72) Inventor: James Sproul, Bakersfield, CA (US)

(73) Assignee: THE CONARD-PYLE COMPANY, West Grove, PA (US)

( * ) Notice: Subject to any disclaimer, the term of this patent is extended or adjusted under 35 U.S.C. 154(b) by 0 days.

(21) Appl. No.: 16/350,676

(22) Filed: Dec. 19, 2018

(51) Int. Cl.
*A01H 5/02* (2018.01)
*A01H 6/74* (2018.01)

(52) U.S. Cl.
USPC ..... Plt./116

(58) Field of Classification Search
USPC ..... Plt./116
CPC ..... A01H 5/02
See application file for complete search history.

*Primary Examiner* — Annette H Para
(74) *Attorney, Agent, or Firm* — Buchanan Ingersoll & Rooney PC

(57) ABSTRACT

A new and distinct variety of miniature rose plant, herein referred to by its cultivar name, 'Sproulsun', is provided which forms abundantly on a substantially continuous basis attractive, cup shaped red striped blossoms. Attractive, semi-glossy, dark green foliage is formed, which contrasts beautifully with the blossoms. The vegetation is vigorous and the growth habit is very bushy and compact. The new variety is well suited for providing attractive ornamentation in the landscape.

2 Drawing Sheets

Botanical/commercial classification:
Latin name—*Rosa hybrida.*
Common name—Miniature Rose Plant.
Varietal denomination: 'Sproulsun'.

SUMMARY OF THE INVENTION

The new variety of *Rosa hybrida* miniature rose plant was created during April of 2012 in Bakersfield, Calif., U.S.A., by artificial pollination wherein two parents were crossed which previously had been studied in the hope that they would contribute the desired characteristics. The female parent (i.e., the seed parent) was an unnamed seedling (non-patented). The male parent (i.e., the pollen parent) was the 'Radtko' variety (U.S. Plant Pat. No. 16,202).

The parentage of the new variety can be summarized as follows:

unnamed seedling x 'Radtko'

The seeds resulting from the above pollination were sown and small plants were obtained which were physically and biologically different from each other. Selective study resulted in the identification of a single plant of the new variety.

It was found that the new variety of miniature rose plant of the present invention possesses the following combination of characteristics:

(a) forms attractive, cup shaped, red striped colored blossoms abundantly and substantially continuously,
(b) exhibits a very bushy and compact growth habit,
(c) forms vigorous vegetation, and
(d) provides attractive ornamental semi-glossy, dark green foliage.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the unnamed seedling female parent (i.e., the seed parent) provides less petals and less concentration of red coloration in the stripes of the blossoms, compared to the new variety and the 'Radtko' variety (i.e., the pollen parent) provides less petals, larger blooms, and has much less compact habit compared to the new variety. Moreover, the new variety can be readily distinguished from other similar non-parental varieties. For example, the 'Stars 'n' Stripes Forever' variety (non-patented in the U.S.) displays less petals, exhibits a less compact growth habit, and is more fragrant compared to the new variety.

The new variety has been found to undergo asexual propagation in Wasco, Calif. by a number of routes, including vegetative cuttings. Asexual propagation by vegetative cuttings in Wasco, Calif. has shown that the characteristics of the new variety are stable and are strictly transmissible by such asexual propagation from one generation to another. Accordingly, the new variety undergoes asexual propagation in a true-to-type manner.

The new variety has been named 'Sproulsun'.

BRIEF DESCRIPTION OF THE PHOTOGRAPH

The accompanying photograph of FIG. 1 shows as nearly true as it is reasonably possible to make the same, in a color illustration of this character, a typical specimen of the new variety. The rose plant of the new variety was approximately two years of age and was observed during June 2017 while growing on its own roots and growing outdoors at Cochranville, Pa., U.S.A.

DETAILED BOTANICAL DESCRIPTION

Figure 1:
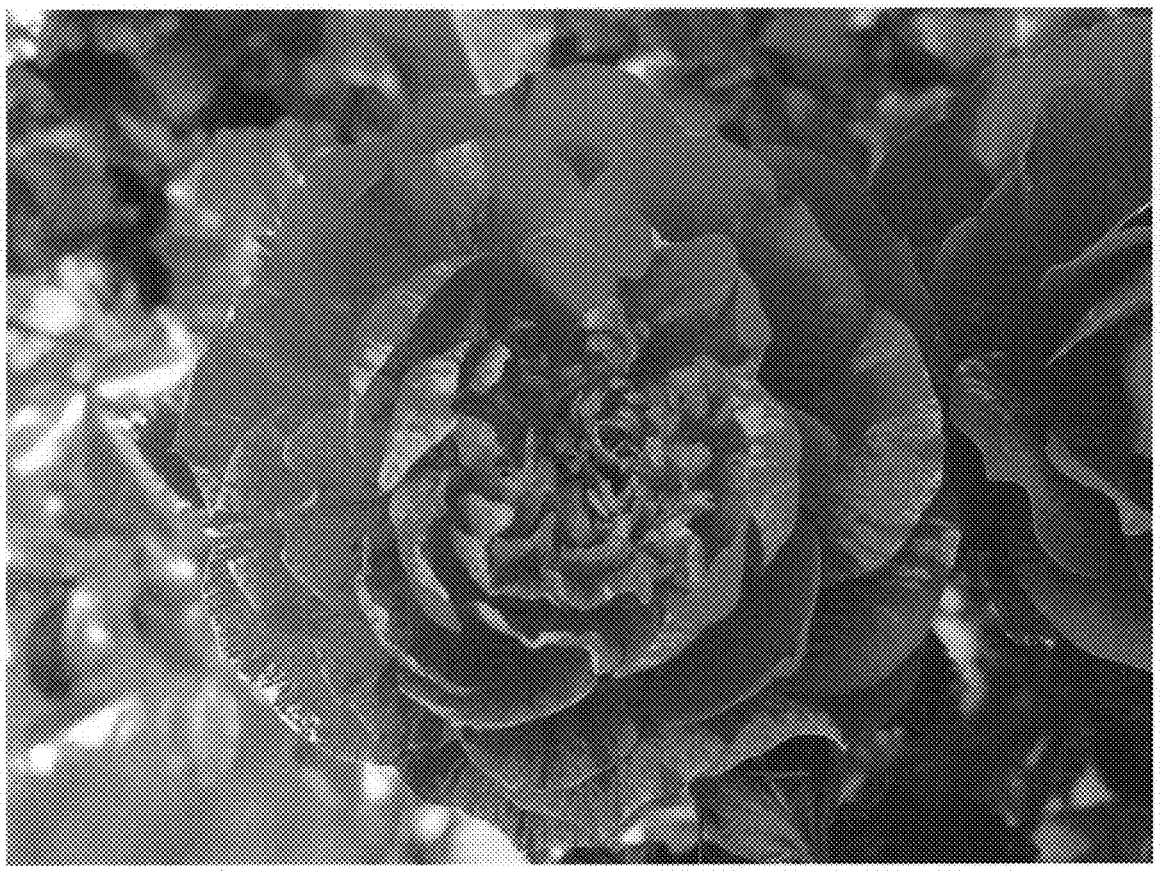
FIG. 1 illustrates a specimen of an open flower—plan view—obverse.
Figure 2:
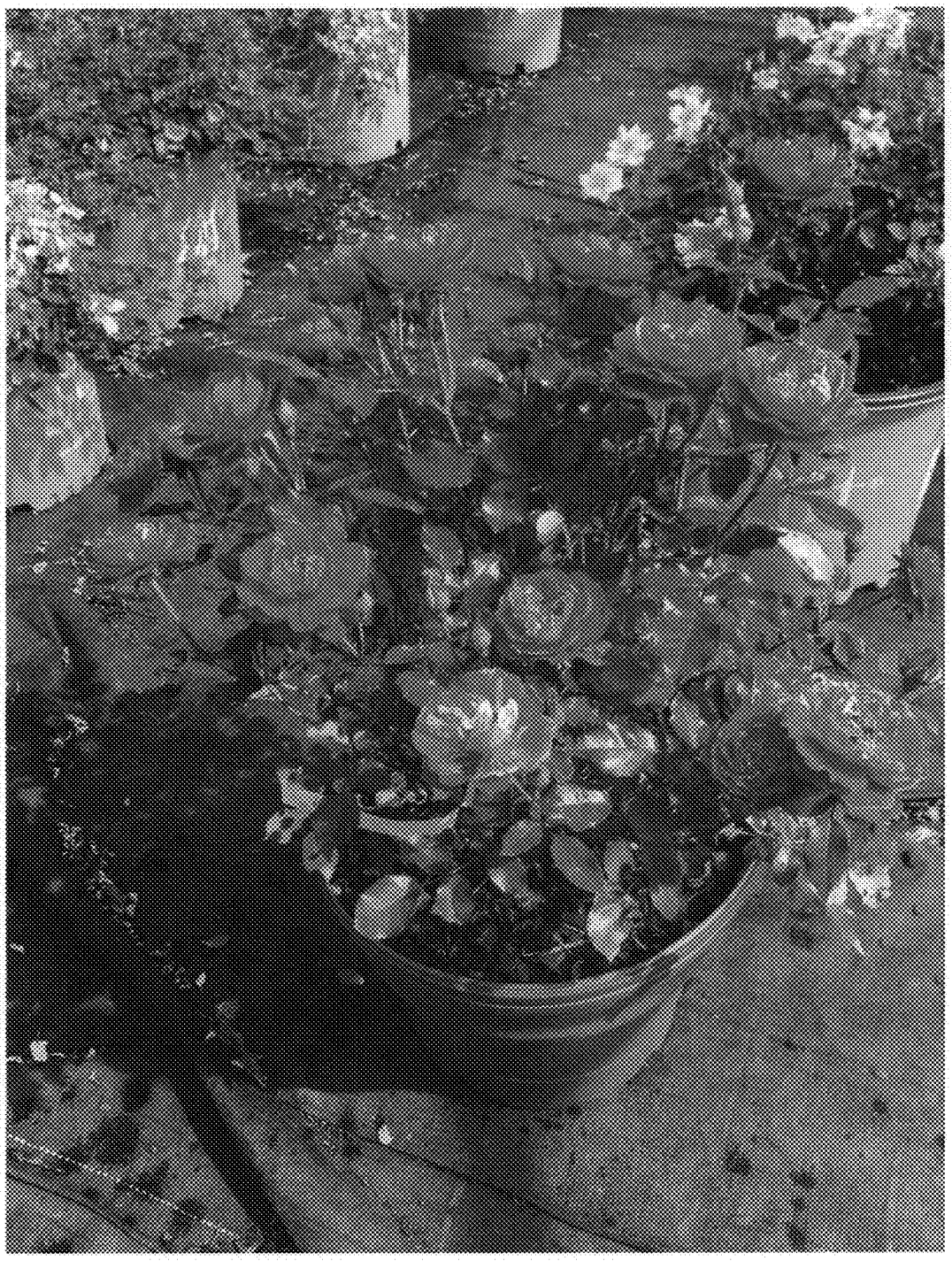
FIG. 2 illustrates a specimen of a whole plant.

The chart used in the identification of the colors is that of The Royal Horticultural Society (R.H.S. Colour Chart, 2015 edition), London, England. The terminology which precedes reference to the chart has been added to indicate the corresponding color in more common terms. The description is based on the observation of two-year-old specimens of the new variety during June while growing on their own roots and growing in a three-gallon container at Cochranville, Pa., U.S.A.

Class: Miniature Rose Plant

Plant:

*Habit*.—Very busy and compact.

*Height in container*.—Approximately 23.0 cm on average.

*Width in container*.—Approximately 28.0 cm on average.

Branches:

*Color*.—Young stems: commonly near Yellow-Green Group 144A mixed with near Greyed-Red Group 181A. — adult wood: commonly near Yellow-Green Group 144A.

*Length*.—Main stems: approximately 23.0 cm on average. — secondary stems: approximately 7.0 cm on average.

*Thorns*.—Young thorns: length is approximately 8.0 mm on average, width is approximately 4.0 mm at point of attachment, and color is commonly near Greyed-Orange Group 174A. — old thorns: length is approximately 1.0 cm on average, width is approximately 7.0 mm on average, and color is commonly near Brown Group N200A at the apex and commonly near Brown Group N200B at the base.

Foliage:

*General appearance*.—Dark green with a semi-glossy aspect.

*Number of leaflets*.—3, 5, and 7.

5-*Leaflet leaf*.—Length: approximately 8.5 cm on average. — width: approximately 5.5 cm on average.

*Young foliage*.—Upper surface color: commonly near Green Group 137A. — under surface color: commonly near Green Group 138B.

*Old foliage*.—Upper surface color: commonly near Green Group 137A. — under surface color: commonly near Green Group 138B.

Leaflets:

*Shape*.—Ovate.

*Texture*.—Upper and under surface is smooth.

*Terminal leaflet*.—Length: approximately 2.5 cm on average. — width: approximately 2.3 cm on average. — blade shape: lanceolate. — blade base shape: rounded. — blade apex shape: acute to aristulate.

*Lower leaflet*.—Length: approximately 2.0 cm on average. — width: approximately 1.5 cm on average.

*Leaf margin*.—Serrate.

*Petiole*.—Upper surface: color is commonly near Red-Purple 59A and texture is smooth. — under surface: color is commonly near Yellow-Green Group 145A and texture is glandular with some small prickles.

*Rachis*.—Color of upper surface: commonly near Red-Purple 59A. — color of under surface: commonly near Yellow-Green Group 145A.

*Stipules*.—Margin: entire to erose. — length: approximately 15.0 mm on average. — width: approximately 6.0 mm on average. — color of upper surface: commonly near Green Group 137C. — color of under surface: commonly near Green Group 137D.

Inflorescence:

*Number of flowers*.—Generally about 10 to 20 blooms on average on a plant at once.

*Number of blooms per stem*.—Generally between 1 to 6 blooms per stem on average.

*Bud*.—Shape: Ovoid. — length: approximately 1.5 cm on average. — width: approximately 1.0 cm on average. — color when opening: commonly between near Red-Purple Group 59A and near Red-Purple 60A.

*Sepals*.—Number: commonly 5 on average. — length: approximately 1.8 cm on average. — width: approximately near 9.0 mm on average. — margin: entire with extensions on two or three sepals measuring approximately 5.0 mm in length on average and 1.0 mm in width on average. — upper surface color and texture: commonly near Green Group 138B, covered in short pubescence. — under surface color and texture: commonly near Yellow-Green Group 144A with some coloring near Greyed-Orange Group 176B towards the apex, puberulent.

*Receptacle*.—Achenes stand on the bottom and wall. — color: commonly near Yellow-Green Group 144B. — diameter: approximately 7.0 mm on average. — surface texture: smooth. — shape: round.

*Peduncle*.—Length: approximately 3.5 cm on average. — diameter: approximately 2.0 mm on average. — surface texture: sparely covered in short, flexible thorns that measure less than 2.0 mm in length. — color: commonly near Green Group 138B.

*Petaloids*.—Number: approximately 10 per flower on average. — color: Upper surface: commonly predominantly near Red-Purple Group 64C with some striping and strippling of near Red-Purple 60B. Under surface: commonly predominantly near Red-Purple Group 64D with some striping and strippling of near Red-Purple 64B. — size: length is approximately 1.5 cm on average and width is approximately 8.0 mm on average. — texture: smooth. — margins: variable, entire to erose. — shape: overall variable, oblong and mostly curving inward; apex is round; and base is cuneate.

*Flower*.—Diameter: approximately 4.5 cm on average. — height: approximately 3.0 cm on average. — duration: flower is on the plant approximately 5 days. — shape: cup shaped. — form: double. — number of petals under normal conditions: approximately 46 petals on average. — shape of the petal: overall: broadly obovate. base: cuneate. apex: slightly cuspidate. — petal length: approximately 5.0 cm on average. — petal width: approximately 5.5 cm on average. — petal margin: entire. — petal drop: good. — fragrance: none noticeable. — color when opening begins: upper and under surfaces: at the point of attachment commonly near Yellow Group 4B transitioning to near Red-Purple Group 61B with stripes on petals of near Red-Purple Group 69D. — color at end of blooming: upper and under surfaces: at the point of attachment commonly near Yellow Group 4D transitioning to near Red-Purple Group 61B with stripes on petals of near Red-Purple Group 69D.

*Stamen*.—Number is approximately 80 on average. — anthers: number is approximately 80 on average and coloration is commonly near Greyed-Orange Group N167. — filaments: length is approximately 1.0 cm on average and coloration is commonly near Yellow-Orange Group 20B.

*Pistils*.—Arrangement is separate and free; number is approximately 43 on average. — styles: length is approximately 5.0 mm on average and coloration is commonly near White Group NN155. — stigmas: diameter is approximately 1.0 mm on average and coloration is commonly near Yellow Group 6A. — pollen: color is commonly near Yellow-Orange Group 21A and a moderate amount is present. — hips/seeds: none observed.

Development:

*Vegetation*.—Vigorous and strong.

*Blooming*.—Abundant and nearly continuous from spring through frost.

*Disease resistance*.—Resistance observed for powdery mildew (*Sphaerotheca pannosa*) and rust (*Phragmidium* spp.).

*Insect resistance/insect susceptibility*.—Not observed.

The new 'Sproulsun' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of Miniature Rose plant characterized by the following combination of characteristics:

(a) forms attractive, cup shaped, red striped colored blossoms abundantly and substantially continuously, (b) exhibits a very bushy and compact growth habit, (c) forms vigorous vegetation, and (d) provides attractive ornamental semi-glossy, dark green foliage;

substantially as herein shown and described.

* * * * *